US00PP09540P

United States Patent [19]

Kester

[11] Patent Number: Plant 9,540

[45] Date of Patent: May 7, 1996

[54] HYBRID TEA ROSE PLANT NAMED 'SPEKES'

[75] Inventor: Peet Kester, Honselerskijk, Netherlands

[73] Assignee: Bear Creek Gardens, Inc., Medford, Oreg.

[21] Appl. No.: 413,534

[22] Filed: Mar. 28, 1995

[51] Int. Cl.[6] ..... A01H 5/00

[52] U.S. Cl. ..... Plt./20

[58] Field of Search ..... Plt./19, 20, 21

[56] References Cited

U.S. PATENT DOCUMENTS

P.P. 9,043 1/1995 Kordes ..... Plt./17

*Primary Examiner*—Howard J. Locker

*Attorney, Agent, or Firm*—Klarquist Sparkman Campbell Leigh & Whinston

[57] ABSTRACT

A mutation of the variety KORcrisette distinct and novel in its brightened flower color but the same in all other respects to the variety KORcrisette.

1 Drawing Sheet

The present invention relates to a new and distinct variety of rose plant of the Hybrid Tea class which was originated by me by discovering a color mutation in the variety KORcrisette, U.S. Plant Pat. No. 9,043.

This mutation was found in a planting of KORcrisette and was recognized as distinct and novel. It was propagated and tested and found to be the same in all respects to KORcrisette except for flower color. The characteristics that are outstanding in this new variety and that distinguish it from its parent, as well as from all other varieties of which I am aware:

Instead of having a main flower color of Orange-Red Group 33A, as KORcrisette, it has flower color Red Group 45B.

Asexual reproduction of this new variety by budding, as performed at Baskoop, The Netherlands, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character, together with a typical flower from KORcrisette which appears immediately above the legend SPEkes and displays the Orange-Red Group 33A color of a KORcrisette flower.

The following is a detailed description of my new rose cultivar with color descriptions using terminology in accordance with The Royal Horticultural Society (London) Colour Chart, except where ordinary dictionary significance of color is indicated.

Parentage: A mutation of the variety KORcrisette, U.S. Plant Pat. No. 9,043.

Classification:

*Botanical.*—*Rosa hybrida.*

*Commercial.*—Hybrid Tea.

FLOWER

Observations made from specimens grown in a greenhouse environment in The Netherlands.

Blooming habit: Continuous.

Bud:

*Size.*—1¼ inches long when the petals start to unfurl.

*Form.*—The bud form is long, pointed ovoid.

*Color.*—When sepals first divide, bud color is Red Group 46A. When half blown, the upper sides of the petals are Red Group 45A; and the lower sides of the petals are close to Red Group 53C.

*Sepals.*—Color: Green Group 138B. Surface texture: Covered in fine hairs. There are three normally to heavily appendaged sepals. There are two unappendaged sepals with hairy edges.

*Receptacle.*—Color: Green Group 143C. Shape: Funnel. Size: Broad (¼" widex ⅜" long). Surface: Smooth.

*Peduncle.*—Length: Medium (2"). Surface: Smooth. Color: Light Geren. Strength: Stiff, erect and heavy.

Bloom:

*Size.*—Medium. Average open size is 3½ inches.

*Borne.*—Singly.

*Stems.*—Medium and strong. Average length is about 18–22 inches.

*Form.*—When first open: High centered. Permanence: Retains its form to the end, outer petals curl back in quill fashion.

*Petalage.*—Number of petals under normal conditions: 25–30.

*Color.*—The upper side of the petals is Red Group 45A. The reverse side of the petals is close to Red Group 53C. The base of each petal has a small Yellow Group 4D half moon at its point of attachment (⅛" by 3/16"). The major color on the upper side is Red Group 45A.

*Variegations.*—Occasional white streak on the guard petals.

*Discoloration.*—The general tonality at the end of the first day: No change. At the end of the third day: No change. By day 7, on the plant there is a general fading to Red Group 45C, then at petal drop to Red Group 45D.

*Fragrance.*—Slight.

Petals:

*Texture.*—Thick.

*Shape.*—Round.

*Form.*—Edges moderately quilled.

*Arrangement.*—Imbricated, with a few small petaloids in the center.

*Persistence.*—Drop off cleanly.

*Lastingness.*—On the plant: Very long (10–12 days). As a cut flower: Very Long (14–16 days).

Reproductive parts:

*Anthers.*—Size: Small. Quantity: Many. Color: Yellow. Arrangement: Regular around styles.

*Filaments.*—Color: Reddish.

*Pollen.*—Color: Lemon Yellow.

*Styles.*—Color: Reddish.

*Stigmas.*—Color: Greenish-White.

Form: Bush.

Growth: Vigorous, upright and branching; at one year in the greenhouse, height is 5 feet and width is 3½ feet. Produces 210–220 cut flowers per square meter per year.

Foliage:

*Number of leaflets on normal mid-stem leaves.*—5.

*Size.*—Medium (5" long×3½ "wide).

*Quantity.*—Abundant.

*Color.*—New foliage: Underside: Greyed Orange Group 176B; Upperside: Greyed Orange Group 176B. Old foliage: Underside: Green Group 139C; Upperside: Green Group 137A.

Leaflets:

*Shape.*—Pointed oval.

*Texture.*—Upper side: Leathery.

*Edge.*—Serrated.

*Serration.*—Single, small.

*Petiole rachis.*—Color: Green.

*Petiole underside.*—Smooth, with usually three small prickles.

*Stipules.*—Medium (½"), serrated and bearded.

*Disease resistance.*—Resistant to mildew under normal greenhouse growing conditions at Somis, Calif.

Wood:

*New wood.*—Color: Light Green. Bark: Smooth.

*Old wood.*—Color: Green. Bark: Smooth.

Prickles:

*Quantity.*—On main canes from base: Ordinary to few. On laterals from main canes: Ordinary to few.

*Form.*—Short (⅛") and straight to slightly hooked downward.

*Color when young.*—Red.

Small prickles:

*Quantity.*—On main stalks: None. On laterals: None:

I claim:

1. A new and distinct variety of rose plant of the Hybrid Tea class, substantially as herein shown and described, characterized particularly as to novelty by the unique combination of its bright red flower color, its excellent production of cut flowers, its long vase life, its thick, leathery petals and its attractive flower form.

* * * * *

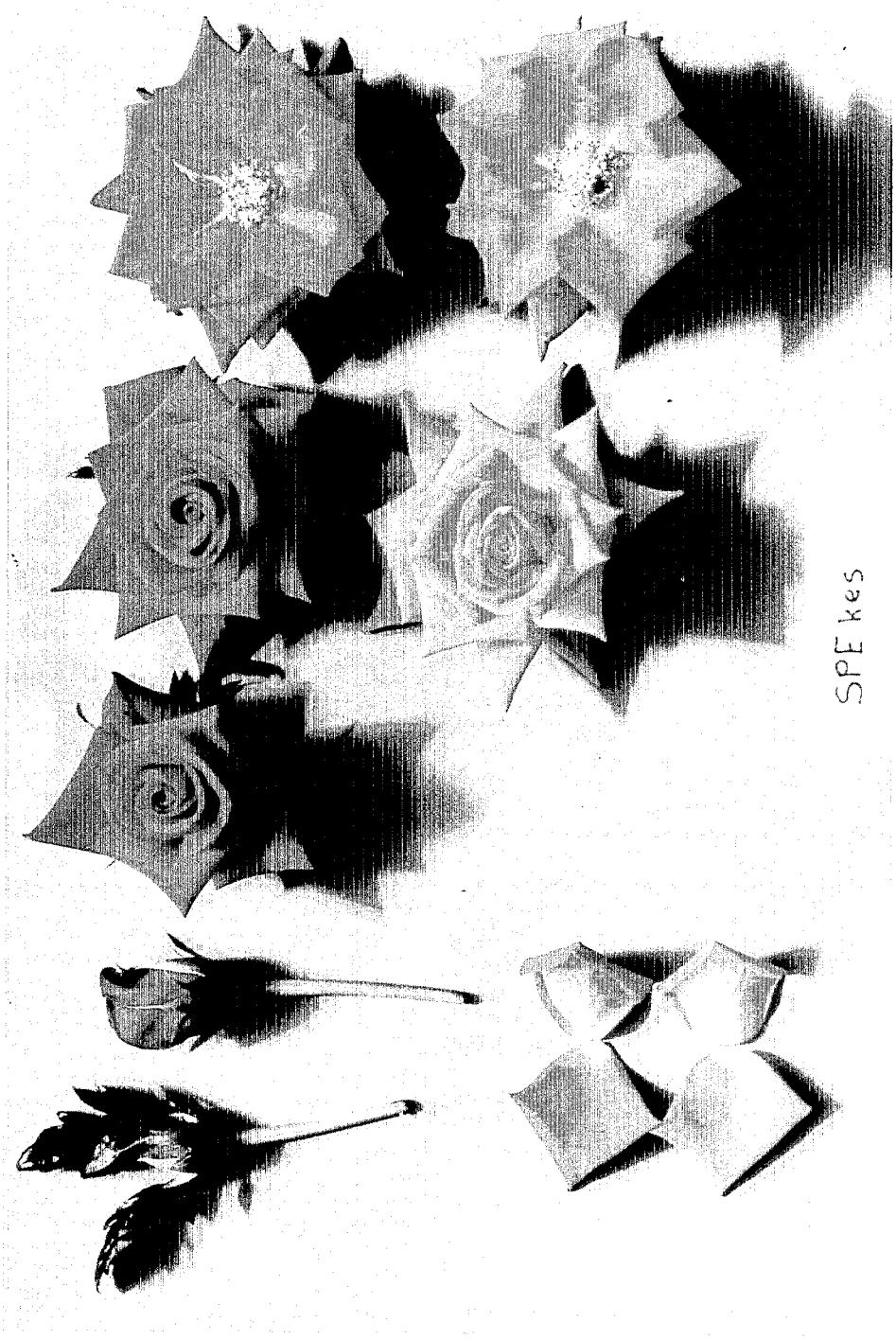
SPE kes

UNITED STATES PATENT AND TRADEMARK OFFICE

CERTIFICATE OF CORRECTION

PATENT NO. : PP 9,540

DATED : May 7, 1996

INVENTOR(S) : Peet Kester

It is certified that error appears in the above-indentified patent and that said Letters Patent is hereby corrected as shown below:

Column 2, line 10, "Geren" should read --Green--.

Column 4, line 14, "None:" should read --None.--.

Signed and Sealed this

Eighth Day of October, 1996

*Attest:*

*Attesting Officer*

BRUCE LEHMAN

*Commissioner of Patents and Trademarks*